(12) United States Patent
Karpiel et al.

(10) Patent No.: US 8,491,610 B2
(45) Date of Patent: Jul. 23, 2013

(54) CLIP DEVICES AND METHODS OF DELIVERY AND DEPLOYMENT

(75) Inventors: John A. Karpiel, Winston-Salem, NC (US); Andres F. Aguirre, Burlington, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 302 days.

(21) Appl. No.: 12/638,190

(22) Filed: Dec. 15, 2009

(65) Prior Publication Data
US 2010/0160935 A1 Jun. 24, 2010

Related U.S. Application Data

(60) Provisional application No. 61/139,141, filed on Dec. 19, 2008.

(51) Int. Cl.
*A61B 17/08* (2006.01)

(52) U.S. Cl.
USPC .......................................... 606/151; 606/142

(58) Field of Classification Search
USPC .................... 606/142, 219–221, 139
See application file for complete search history.

(56) References Cited

U.S. PATENT DOCUMENTS

| | | | |
|---|---|---|---|
| 2,199,025 A | 4/1940 | Conn |
| 2,671,444 A | 3/1954 | Pease, Jr. |
| 3,209,422 A | 10/1965 | Dritz |
| 3,399,432 A | 9/1968 | Merser |
| 3,470,834 A | 10/1969 | Bone |
| 3,556,079 A | 1/1971 | Omizo |
| 3,814,104 A | 6/1974 | Irnich et al. |
| 3,856,016 A | 12/1974 | Davis |
| 3,954,108 A | 5/1976 | Davis |

(Continued)

FOREIGN PATENT DOCUMENTS

| | | |
|---|---|---|
| EP | 0310582 A1 | 4/1989 |
| EP | 0774237 A2 | 5/1997 |

(Continued)

OTHER PUBLICATIONS

Communication Pursuant to Rules 161(1) and 162EPC for European Patent Application Serial No. 09791618.3, dated Mar. 28, 2011, 2 pages.

(Continued)

*Primary Examiner* — Darwin Erezo
*Assistant Examiner* — Alexander Orkin
(74) *Attorney, Agent, or Firm* — Brinks Hofer Gilson & Lione

(57) ABSTRACT

The present embodiments provide a clip device for engaging tissue. The clip device comprises at least first and second arms having proximal and distal ends. The clip device comprises an open state when a spring member is in a compressed state in which the distal end of the spring member is spaced further apart from the distal ends of the first and second arms. In the open state, the distal ends of the first and second arms tend to be spaced apart from each other. Further, the clip device comprises a closed state when the spring member is in a relaxed state in which the spring member is biased to extend distally and the distal ends of the first and second arms are adjacent to each other and may engage tissue and promote hemostatis. A delivery system and methods for deploying one or more clip devices also are provided.

20 Claims, 5 Drawing Sheets

U.S. PATENT DOCUMENTS

| | | | |
|---|---|---|---|
| 3,958,576 | A | 5/1976 | Komiya |
| 4,006,747 | A | 2/1977 | Kronenthal et al. |
| 4,204,541 | A | 5/1980 | Kapitanov |
| 4,217,902 | A | 8/1980 | March |
| 4,235,238 | A | 11/1980 | Ogiu et al. |
| 4,485,816 | A | 12/1984 | Krumme |
| 4,621,639 | A | 11/1986 | Transue et al. |
| 4,749,114 | A | 6/1988 | Green |
| 4,773,420 | A | 9/1988 | Green |
| 4,791,707 | A | 12/1988 | Tucker |
| 4,796,627 | A | 1/1989 | Tucker |
| 4,821,939 | A | 4/1989 | Green |
| 4,832,027 | A | 5/1989 | Utz |
| 4,990,156 | A | 2/1991 | Lefebvre |
| 5,015,249 | A | 5/1991 | Nakao et al. |
| 5,049,153 | A | 9/1991 | Nakao et al. |
| 5,059,205 | A | 10/1991 | El-Nounou et al. |
| 5,084,057 | A | 1/1992 | Green et al. |
| 5,099,827 | A | 3/1992 | Melzer et al. |
| 5,100,418 | A * | 3/1992 | Yoon et al. .................. 606/139 |
| 5,100,420 | A | 3/1992 | Green et al. |
| 5,123,914 | A | 6/1992 | Cope |
| 5,156,609 | A | 10/1992 | Nakao et al. |
| 5,192,303 | A | 3/1993 | Gatturna et al. |
| 5,203,787 | A | 4/1993 | Noblitt et al. |
| 5,242,456 | A | 9/1993 | Nash et al. |
| 5,324,307 | A | 6/1994 | Jarrett et al. |
| 5,333,624 | A | 8/1994 | Tovey |
| 5,334,217 | A | 8/1994 | Das |
| 5,350,385 | A | 9/1994 | Christy |
| 5,366,480 | A | 11/1994 | Corriveau et al. |
| 5,368,600 | A | 11/1994 | Failla et al. |
| 5,368,602 | A | 11/1994 | de la Torre |
| 5,411,522 | A | 5/1995 | Trott |
| 5,417,691 | A | 5/1995 | Hayhurst |
| 5,437,266 | A | 8/1995 | McPherson |
| 5,520,700 | A | 5/1996 | Beyar et al. |
| 5,527,343 | A | 6/1996 | Bonutti |
| 5,554,183 | A | 9/1996 | Nazari |
| 5,573,543 | A | 11/1996 | Akopov et al. |
| 5,582,615 | A | 12/1996 | Foshee et al. |
| 5,582,616 | A | 12/1996 | Bolduc et al. |
| 5,593,414 | A | 1/1997 | Shipp et al. |
| 5,662,683 | A | 9/1997 | Kay |
| 5,667,527 | A | 9/1997 | Cook et al. |
| 5,674,231 | A | 10/1997 | Green et al. |
| 5,690,656 | A | 11/1997 | Cope et al. |
| 5,695,525 | A | 12/1997 | Mulhauser et al. |
| 5,728,116 | A | 3/1998 | Rosenman |
| 5,741,278 | A | 4/1998 | Stevens |
| 5,779,720 | A | 7/1998 | Walder-Utz et al. |
| 5,810,848 | A | 9/1998 | Hayhurst |
| 5,865,791 | A | 2/1999 | Whayne et al. |
| 5,868,763 | A | 2/1999 | Spence et al. |
| 5,891,159 | A | 4/1999 | Sherman et al. |
| 5,968,078 | A | 10/1999 | Grotz |
| 5,972,002 | A | 10/1999 | Bark et al. |
| 5,972,022 | A | 10/1999 | Huxel |
| 5,976,159 | A | 11/1999 | Bolduc et al. |
| 5,984,917 | A | 11/1999 | Fleischman et al. |
| 5,984,949 | A | 11/1999 | Levin |
| 6,110,183 | A | 8/2000 | Cope |
| 6,113,612 | A | 9/2000 | Swanson et al. |
| RE36,974 | E | 11/2000 | Bonutti |
| 6,149,658 | A | 11/2000 | Gardiner et al. |
| 6,152,935 | A | 11/2000 | Kammerer et al. |
| 6,152,937 | A | 11/2000 | Peterson et al. |
| 6,156,044 | A | 12/2000 | Kammerer et al. |
| 6,159,223 | A | 12/2000 | Danks et al. |
| 6,171,321 | B1 | 1/2001 | Gifford, III et al. |
| 6,183,486 | B1 | 2/2001 | Snow et al. |
| 6,193,732 | B1 | 2/2001 | Frantzen et al. |
| 6,228,055 | B1 | 5/2001 | Foerster et al. |
| 6,241,747 | B1 | 6/2001 | Ruff |
| 6,290,674 | B1 | 9/2001 | Roue et al. |
| 6,306,150 | B1 | 10/2001 | Levinson |
| 6,328,727 | B1 | 12/2001 | Frazier et al. |
| 6,371,963 | B1 | 4/2002 | Nishtala et al. |
| 6,402,765 | B1 | 6/2002 | Monassevitch et al. |
| 6,419,669 | B1 | 7/2002 | Frazier et al. |
| 6,425,887 | B1 | 7/2002 | McGuckin et al. |
| 6,425,900 | B1 | 7/2002 | Knodel et al. |
| 6,428,548 | B1 | 8/2002 | Durgin et al. |
| 6,446,854 | B1 | 9/2002 | Remiszewski et al. |
| 6,447,530 | B1 | 9/2002 | Ostrovsky et al. |
| 6,468,290 | B1 | 10/2002 | Weldon et al. |
| 6,482,178 | B1 | 11/2002 | Andrews et al. |
| 6,491,707 | B2 | 12/2002 | Makower et al. |
| 6,551,333 | B2 | 4/2003 | Kuhns et al. |
| 6,572,629 | B2 | 6/2003 | Kalloo et al. |
| 6,592,559 | B1 | 7/2003 | Pakter et al. |
| 6,623,510 | B2 | 9/2003 | Carley et al. |
| 6,641,557 | B1 | 11/2003 | Frazier et al. |
| 6,699,256 | B1 | 3/2004 | Logan et al. |
| 6,699,263 | B2 | 3/2004 | Cope |
| 6,712,804 | B2 | 3/2004 | Roue et al. |
| 6,719,777 | B2 | 4/2004 | Ginn et al. |
| 6,746,458 | B1 | 6/2004 | Cloud |
| 6,746,460 | B2 | 6/2004 | Gannoe et al. |
| 6,746,472 | B2 | 6/2004 | Frazier et al. |
| 6,776,783 | B1 | 8/2004 | Frantzen et al. |
| 6,849,078 | B2 | 2/2005 | Durgin et al. |
| 6,884,248 | B2 | 4/2005 | Bolduc et al. |
| 6,911,032 | B2 | 6/2005 | Jugenheimer et al. |
| 6,913,607 | B2 | 7/2005 | Ainsworth et al. |
| 6,966,916 | B2 | 11/2005 | Kumar |
| 6,994,713 | B2 | 2/2006 | Berg et al. |
| 7,001,398 | B2 | 2/2006 | Carley et al. |
| 7,018,388 | B2 | 3/2006 | Yencho et al. |
| 7,025,756 | B2 | 4/2006 | Frazier et al. |
| 7,056,325 | B1 | 6/2006 | Makower et al. |
| 7,060,084 | B1 | 6/2006 | Loshakove et al. |
| 7,087,073 | B2 | 8/2006 | Bonutti |
| 7,112,214 | B2 | 9/2006 | Peterson et al. |
| 7,115,110 | B2 | 10/2006 | Frazier et al. |
| 7,211,101 | B2 | 5/2007 | Carley et al. |
| 7,326,221 | B2 | 2/2008 | Sakamoto |
| 7,326,231 | B2 | 2/2008 | Phillips et al. |
| 7,331,968 | B2 | 2/2008 | Arp et al. |
| 7,410,460 | B2 | 8/2008 | Benderev |
| 7,416,554 | B2 | 8/2008 | Lam et al. |
| 7,485,124 | B2 | 2/2009 | Kuhns et al. |
| 7,494,496 | B2 | 2/2009 | Swain et al. |
| 7,601,159 | B2 | 10/2009 | Ewers et al. |
| 7,608,091 | B2 | 10/2009 | Goldfarb et al. |
| 7,618,426 | B2 | 11/2009 | Ewers et al. |
| 7,621,925 | B2 | 11/2009 | Saadat et al. |
| 7,622,068 | B2 | 11/2009 | Li et al. |
| 7,641,836 | B2 | 1/2010 | Li et al. |
| 7,655,015 | B2 | 2/2010 | Goldfarb et al. |
| 7,666,197 | B2 | 2/2010 | Orban, III |
| 7,670,362 | B2 | 3/2010 | Zergiebel |
| 7,695,493 | B2 | 4/2010 | Saadat et al. |
| 7,704,264 | B2 | 4/2010 | Ewers et al. |
| 7,722,628 | B2 | 5/2010 | Stokes et al. |
| 7,727,247 | B2 | 6/2010 | Kimura et al. |
| 7,727,248 | B2 | 6/2010 | Smith et al. |
| 7,736,376 | B2 | 6/2010 | Sato et al. |
| 7,736,378 | B2 | 6/2010 | Maahs et al. |
| 7,736,379 | B2 | 6/2010 | Ewers et al. |
| 7,736,388 | B2 | 6/2010 | Goldfarb et al. |
| 7,744,613 | B2 | 6/2010 | Ewers et al. |
| 7,758,598 | B2 | 7/2010 | Conlon et al. |
| 7,758,612 | B2 | 7/2010 | Shipp |
| 7,799,040 | B2 | 9/2010 | Stokes et al. |
| 7,803,165 | B2 | 9/2010 | Stokes et al. |
| 7,803,166 | B2 | 9/2010 | Stokes et al. |
| 7,815,652 | B2 | 10/2010 | Messerly et al. |
| 7,815,653 | B2 | 10/2010 | Stokes et al. |
| 7,815,659 | B2 | 10/2010 | Conlon et al. |
| 7,815,662 | B2 | 10/2010 | Spivey et al. |
| 7,828,811 | B2 | 11/2010 | Kortenbach et al. |
| 2001/0002250 | A1 | 5/2001 | Burbank et al. |
| 2001/0037130 | A1 | 11/2001 | Adams |
| 2001/0039435 | A1 | 11/2001 | Roue et al. |
| 2003/0158578 | A1 | 8/2003 | Pantages et al. |
| 2003/0195561 | A1 | 10/2003 | Carley et al. |

| | | | | | | |
|---|---|---|---|---|---|---|
| 2004/0009289 A1 | 1/2004 | Carley et al. | | 2008/0208214 A1 | 8/2008 | Sato et al. |
| 2004/0039414 A1 | 2/2004 | Carley et al. | | 2008/0208218 A1 | 8/2008 | Shiono |
| 2004/0044364 A1 | 3/2004 | Devries et al. | | 2008/0208219 A1 | 8/2008 | Suzuki |
| 2004/0073236 A1 | 4/2004 | Carley et al. | | 2008/0208220 A1 | 8/2008 | Shiono et al. |
| 2004/0087981 A1 | 5/2004 | Berube et al. | | 2008/0208251 A1 | 8/2008 | Weadock et al. |
| 2004/0087985 A1 | 5/2004 | Loshakove et al. | | 2008/0221619 A1 | 9/2008 | Spivey et al. |
| 2004/0092975 A1 | 5/2004 | Loshakove et al. | | 2008/0228199 A1 | 9/2008 | Cropper et al. |
| 2004/0097982 A1 | 5/2004 | Jugenheimer et al. | | 2008/0228202 A1 | 9/2008 | Cropper et al. |
| 2004/0167539 A1 | 8/2004 | Kuehn et al. | | 2008/0228203 A1 | 9/2008 | Bell et al. |
| 2004/0186514 A1 | 9/2004 | Swain et al. | | 2008/0243148 A1 | 10/2008 | Mikkaichi et al. |
| 2004/0220596 A1 | 11/2004 | Frazier et al. | | 2008/0255422 A1 | 10/2008 | Kondoh et al. |
| 2005/0015141 A1 | 1/2005 | Quiachon et al. | | 2008/0255423 A1 | 10/2008 | Kondo et al. |
| 2005/0033313 A1 | 2/2005 | Chu et al. | | 2008/0262525 A1 | 10/2008 | Chang et al. |
| 2005/0038370 A1 | 2/2005 | Kuth et al. | | 2008/0269566 A1 | 10/2008 | Measamer |
| 2005/0059985 A1* | 3/2005 | Kimura .................... 606/151 | | 2008/0275297 A1 | 11/2008 | Bakos et al. |
| 2005/0113851 A1 | 5/2005 | Swain et al. | | 2008/0281354 A1 | 11/2008 | Cropper et al. |
| 2005/0119695 A1 | 6/2005 | Carley et al. | | 2008/0294178 A1 | 11/2008 | Kortenbach et al. |
| 2005/0143763 A1 | 6/2005 | Ortiz et al. | | 2008/0296344 A1 | 12/2008 | Cropper et al. |
| 2005/0171562 A1 | 8/2005 | Criscuolo et al. | | 2008/0300547 A1 | 12/2008 | Bakos |
| 2005/0182426 A1* | 8/2005 | Adams et al. .................. 606/142 | | 2008/0300608 A1 | 12/2008 | Measamer |
| 2005/0182445 A1 | 8/2005 | Zamierowski | | 2008/0300624 A1 | 12/2008 | Schwemberger et al. |
| 2005/0192596 A1 | 9/2005 | Jugenheimer et al. | | 2008/0300627 A1 | 12/2008 | Measamer et al. |
| 2005/0197594 A1 | 9/2005 | Burbank et al. | | 2008/0319257 A1 | 12/2008 | Sato et al. |
| 2005/0234512 A1 | 10/2005 | Nakao | | 2009/0005800 A1 | 1/2009 | Franer et al. |
| 2005/0251165 A1 | 11/2005 | Vaughan et al. | | 2009/0018552 A1 | 1/2009 | Lam et al. |
| 2005/0277945 A1 | 12/2005 | Saadat et al. | | 2009/0069822 A1 | 3/2009 | Takahashi et al. |
| 2005/0277981 A1 | 12/2005 | Maahs et al. | | 2009/0088780 A1 | 4/2009 | Shiono et al. |
| 2005/0283188 A1 | 12/2005 | Loshakove et al. | | 2009/0088797 A1 | 4/2009 | Crombie et al. |
| 2006/0004409 A1 | 1/2006 | Nobis et al. | | 2009/0125038 A1 | 5/2009 | Ewers et al. |
| 2006/0004410 A1 | 1/2006 | Nobis et al. | | 2009/0125039 A1 | 5/2009 | Mikkaichi et al. |
| 2006/0015006 A1 | 1/2006 | Laurence et al. | | 2009/0204147 A1 | 8/2009 | Rahmani |
| 2006/0015125 A1 | 1/2006 | Swain | | 2009/0222029 A1 | 9/2009 | Gordin et al. |
| 2006/0025788 A1 | 2/2006 | Loshakove et al. | | 2009/0287080 A1 | 11/2009 | Nishina et al. |
| 2006/0025819 A1 | 2/2006 | Nobis et al. | | 2009/0299385 A1 | 12/2009 | Stefanchik et al. |
| 2006/0106279 A1 | 5/2006 | Machold et al. | | 2009/0299406 A1 | 12/2009 | Swain et al. |
| 2006/0106405 A1 | 5/2006 | Fann et al. | | 2009/0306686 A1 | 12/2009 | Ohdaira |
| 2006/0116605 A1 | 6/2006 | Nakao | | 2009/0318936 A1 | 12/2009 | Harris et al. |
| 2006/0135989 A1 | 6/2006 | Carley et al. | | 2009/0326578 A1 | 12/2009 | Ewers et al. |
| 2006/0155288 A1 | 7/2006 | Little et al. | | 2010/0010457 A1 | 1/2010 | Ewers et al. |
| 2006/0167484 A1 | 7/2006 | Carley et al. | | 2010/0010508 A1 | 1/2010 | Takahashi et al. |
| 2006/0190016 A1 | 8/2006 | Onuki et al. | | 2010/0010509 A1 | 1/2010 | Ishioka et al. |
| 2006/0190038 A1 | 8/2006 | Carley et al. | | 2010/0010511 A1 | 1/2010 | Harris et al. |
| 2006/0206063 A1 | 9/2006 | Kagan et al. | | 2010/0010514 A1 | 1/2010 | Ishioka et al. |
| 2006/0207606 A1 | 9/2006 | Roue et al. | | 2010/0010520 A1 | 1/2010 | Takahashi et al. |
| 2006/0217762 A1 | 9/2006 | Maahs et al. | | 2010/0042115 A1 | 2/2010 | Saadart et al. |
| 2006/0235447 A1 | 10/2006 | Walshe | | 2010/0042144 A1 | 2/2010 | Bennett |
| 2006/0237022 A1 | 10/2006 | Chen et al. | | 2010/0049244 A1 | 2/2010 | Cohen et al. |
| 2006/0237023 A1 | 10/2006 | Cox et al. | | 2010/0076462 A1 | 3/2010 | Bakos et al. |
| 2006/0241662 A1 | 10/2006 | Adams et al. | | 2010/0076488 A1 | 3/2010 | Spivey et al. |
| 2006/0241691 A1 | 10/2006 | Wilk | | 2010/0094341 A1 | 4/2010 | Raju |
| 2006/0253144 A1 | 11/2006 | Mikkaichi et al. | | 2010/0106166 A1 | 4/2010 | Cropper et al. |
| 2006/0271073 A1 | 11/2006 | Lam et al. | | 2010/0113873 A1 | 5/2010 | Suzuki et al. |
| 2006/0271101 A1 | 11/2006 | Saadat et al. | | 2010/0121351 A1 | 5/2010 | Whitfield et al. |
| 2007/0010835 A1 | 1/2007 | Breton et al. | | 2010/0174312 A1 | 7/2010 | Maahs et al. |
| 2007/0100375 A1 | 5/2007 | Mikkaichi et al. | | 2010/0198192 A1 | 8/2010 | Serina et al. |
| 2007/0100376 A1 | 5/2007 | Mikkaichi et al. | | 2010/0211086 A1 | 8/2010 | Ewers et al. |
| 2007/0112362 A1 | 5/2007 | Mikkaichi et al. | | 2010/0217292 A1 | 8/2010 | Kimura et al. |
| 2007/0123840 A1 | 5/2007 | Cox | | 2010/0217293 A1 | 8/2010 | Kimura et al. |
| 2007/0129755 A1 | 6/2007 | Abbott et al. | | 2010/0217294 A1 | 8/2010 | Kimura et al. |
| 2007/0173868 A1 | 7/2007 | Bachinski et al. | | 2010/0249498 A1 | 9/2010 | Wingardner et al. |
| 2007/0208360 A1 | 9/2007 | Demarais et al. | | 2010/0256658 A1 | 10/2010 | Criscuolo et al. |
| 2007/0219411 A1 | 9/2007 | Dejima et al. | | 2010/0264192 A1 | 10/2010 | Marczyk |
| 2007/0270752 A1 | 11/2007 | LaBombard | | 2010/0268253 A1 | 10/2010 | Ahlberg et al. |
| 2007/0270943 A1 | 11/2007 | Solem et al. | | 2010/0268270 A1 | 10/2010 | Viola |
| 2007/0276416 A1 | 11/2007 | Ginn et al. | | 2011/0022065 A1 | 1/2011 | Shipp |
| 2007/0276424 A1 | 11/2007 | Mikkaichi et al. | | | | |
| 2007/0282355 A1* | 12/2007 | Brown et al. .................. 606/151 | | FOREIGN PATENT DOCUMENTS | | |
| 2008/0015633 A1 | 1/2008 | Abbott et al. | | | | |
| 2008/0086153 A1 | 4/2008 | Sakamoto et al. | | EP | 1317904 A1 | 11/2003 |
| 2008/0091059 A1 | 4/2008 | Machold | | EP | 1961388 A2 | 8/2008 |
| 2008/0097489 A1 | 4/2008 | Goldfarb et al. | | WO | WO88/01486 | 3/1988 |
| 2008/0114378 A1 | 5/2008 | Matsushita | | WO | WO90/02522 | 3/1990 |
| 2008/0114398 A1 | 5/2008 | Phillips et al. | | WO | WO95/21575 | 8/1995 |
| 2008/0147116 A1 | 6/2008 | Smith et al. | | WO | WO96/14020 | 5/1996 |
| 2008/0154290 A1 | 6/2008 | Golden et al. | | WO | WO96/40356 | 12/1996 |
| 2008/0172088 A1 | 7/2008 | Smith et al. | | WO | WO98/18389 | 5/1998 |
| 2008/0177304 A1 | 7/2008 | Westra et al. | | WO | WO99/62408 | 12/1999 |
| 2008/0200930 A1 | 8/2008 | Saadat et al. | | WO | WO00/07506 | 2/2000 |
| 2008/0208161 A1 | 8/2008 | Kaji et al. | | WO | WO00/16701 | 3/2000 |
| | | | | WO | WO00/21443 | 4/2000 |

| WO | WO00/56223 | 9/2000 |
| WO | WO00/56227 | 9/2000 |
| WO | WO01/19256 | 3/2001 |
| WO | WO01/35832 | 5/2001 |
| WO | WO01/58363 | 8/2001 |
| WO | WO2005/034729 | 4/2005 |
| WO | WO2007/004228 | 1/2007 |
| WO | WO2007/024615 | 3/2007 |
| WO | WO2007/089843 | 8/2007 |
| WO | WO2007/142977 | 12/2007 |

OTHER PUBLICATIONS

Response to Communication Pursuant to Rules 161(1) and 162EPC for European Patent Application Serial No. 09791618.3, dated May 6, 2011, 4 pages.
International Search Report for PCT/US2009/041415, dated Jul. 24, 2009, 4 pages.
International Preliminary Report on Patentability for PCT/US2009/041415, dated Nov. 4, 2010, 6 pages.
International Search Report for PCT/US2009/054176, dated Nov. 20, 2009, 16 pages.
International Preliminary Report on Patentability for PCT/US2009/054176, dated Mar. 3, 2011, 9 pages.
International Search Report for PCT/US2009/056512, dated Feb. 10, 2010, 5 pages.
Article 34 Demand and Amendment for PCT/US2009/056512, dated Jul. 6, 2010, 22 pages.
International Preliminary Report on Patentability for PCT/US2009/056512, dated Jan. 10, 2010, 31 pages.
International Search Report and Written Opinion for PCT/US2009/056604, dated May 4, 2010, 9 pages.
International Search Report for PCT/US2009/066983, dated Jan. 19, 2010, 4 pages.
International Search Report and Written Opinion for PCT/US2009/066992, dated Mar. 4, 2010, 15 pages.
International Search Report and Written Opinion for PCT/US2009/067992, Jul. 9, 2010, 20 pages.
International Search Report and Written Opinion for PCT/US2009/067994, dated Jun. 10, 2010, 18 pages.
International Search Report and Written Opinion for PCT/US2010/036188, dated Sep. 14, 2010, 18 pages.
Restriction Requirement for U.S. Appl. No. 12/428,226, dated Apr. 27, 2011, 7 pages.
Response to Restriction Requirement for U.S. Appl. No. 12/428,226, dated May 27, 2011, 10 pages.
Office Action for U.S. Appl. No. 12/428,226, dated Jun. 9, 2011, 8 pages.
Office Action for U.S. Appl. No. 12/543,000, dated Mar. 15, 2011, 14 pages.
Fritscher-Ravens, "Transgastric endoscopy—a new fashion, a new excitement!", *Endoscopy*, vol. 39, 2007, pp. 161-167.
Sporn et al., "Endoscopic colotomy closure after full thickness excision: comparison of T fastener with mutliclip applier", *Endoscopy*, vol. 40, 2008, pp. 589-594.
Voermans et al., "In vitro comparison and evaluation of seven gastric closure modalities for natural orifice transluminal endoscopic surgery", *Endoscopy*, vol. 40, 2008, pp. 595-601.
Sclabas et al., "Endoluminal Methods for Gastrotomy Closure in Natural Orifice TransEnteric Surgery", *Surgical Innovation*, vol. 13, No. 1, Mar. 2006, pp. 23-30.
Desilets et al., "Loop-anchor purse-string versus endoscopic clips for gastric closure: a natural orifice transluminal endoscopic surgery comparison study using burst pressures", *Gastrointestinal Endoscopy*, vol. 70, No. 6, 2009, pp. 1225-1230.
Sporn et al., "Endoscopic colotomy closure for natural orifice transluminal endoscopic surgery using a T-fastener protoype in comparison to conventional laparoscopic suture closure", *Gastrointestinal Endoscopy*, vol. 68, No. 4, 2008, pp. 724-730.

Dray et al., "Air and fluid leak tests after NOTES procedures: a pilot study in a live porcine model", *Gastrointestinal Endoscopy*, vol. 68, No. 3, 2008, pp. 513-519.
Shurr et al., "An over-the-scope clip (OTSC) system for closure of iatrogenic colon perforations: results of an experimental survival study in pigs", *Endoscopy*, vol. 40, 2008, pp. 584-588.
Romanelli et al, "Natural orifice transluminal endoscopic surgery gastrotomy closure in porcine explants with the Padlock-G clip using the Lock-It system", *Endoscopy*, vol. 42, 2010, pp. 306-310.
Bergström et al., "Early clinical experience with a new flexible endoscopic suturing method for natural orifice transluminal endoscopic surgery and intraluminal endosurgery", *Gastrointestinal Endoscopy*, vol. 67, No. 3, 2008, pp. 528-533.
Park et al, "Endoscopic sutured closure of a gastric natural orifice transluminal endoscopic surgery access gastronomy compared with open surgical closure in a porcine model. A randomized, multicenter controlled trial", *Endoscopy*, vol. 42, 2010 pp. 311-317.
Yasser M. Bhat, MD, "Transluminal Endosurgery: Novel Use of Endoscopic Tacks for the Closure of Access Sites in Natural Orifice Transluminal Endoscopic Surgery," *Gastrointestinal Endoscopy*, vol. 69, No. 6, p. 1161.
Patent Examination Report for Australian Patent Application No. 2009335901 issued Oct. 4, 2012; 6 pgs.
Reply to Communication for European Patent Application No. 09796190.8 dated Apr. 12, 2012, 17 pgs.
Response to Restriction Requirement for U.S. Appl. No. 12/428,226 dated May 27, 2011, 7 pgs.
Office Action for U.S. Appl. No. 12/428,226 dated Jun. 9, 2011, 8 pgs.
Response to Office Action for U.S. Appl. No. 12/428,226 dated dated Sep. 9, 2011, 11 pgs.
Final Office Action for U.S. Appl. No. 12/428,226 dated Dec. 9, 2011, 10 pgs.
Notice of Abandonment for U.S. Appl. No. 12/428,226 dated Jun. 21, 2012, 3 pgs.
Response to Office Action for U.S. Appl. No. 12/543,000 dated Jun. 15, 2011, 10 pgs.
Final Office Action for U.S. Appl. No. 12/543,000 dated Sep. 1, 2011, 13 pgs.
Applicant Initiated Interview Summary for U.S. Appl. No. 12/543,000 dated Feb. 3, 2012, 3 pgs.
RCE with Preliminary Amendment for U.S. Appl. No. 12/543,000 dated Feb. 29, 2012, 10 pgs.
Written Opinion for PCT/US2009/041415 dated Jul. 15, 2009, 6 pgs.
Written Opinion for PCT/US2009/056512 dated Mar. 11, 2011, 7 pgs.
International Preliminary Report on Patentability for PCT/US2009/056604 dated Jun. 29, 2011, 6 pgs.
Written Opinion for PCT/US2009/066983 dated Jun. 9, 2011, 7 pgs.
International Preliminary Report on Patentability for PCT/US2009/066983 dated Jun. 14, 2011, 8 pgs.
International Preliminary Report on Patentability for PCT/US2009/066992 date Jun. 14, 2011, 7 pgs.
International Preliminary Report on Patentability for PCT/US2009/067992 dated Jun. 21, 2011, 11 pgs.
International Preliminary Report on Patentability for PCT/US2009/067994 dated Jun. 21, 2011, 10 pgs.
International Preliminary Report on Patentabililty for PCT/US2010/036188 dated Nov. 29, 2011, 9 pgs.
Response to Communication Pursuant to Rule 161(1) and 162EPC for European Patent Application Serial No. 09791618.3 dated May 6, 2011, 4 pgs.
Communication Pursuant to Rule 161(1) and 162EPC for European Patent Application Serial No. 09796190.8 dated Oct. 12, 2011, 2 pgs.
Response to Communication Pursuant to Rule 161(1) and 162EPC for European Patent Application Serial No. 09796190.8 dated Apr. 12, 2012, 18pgs.

* cited by examiner

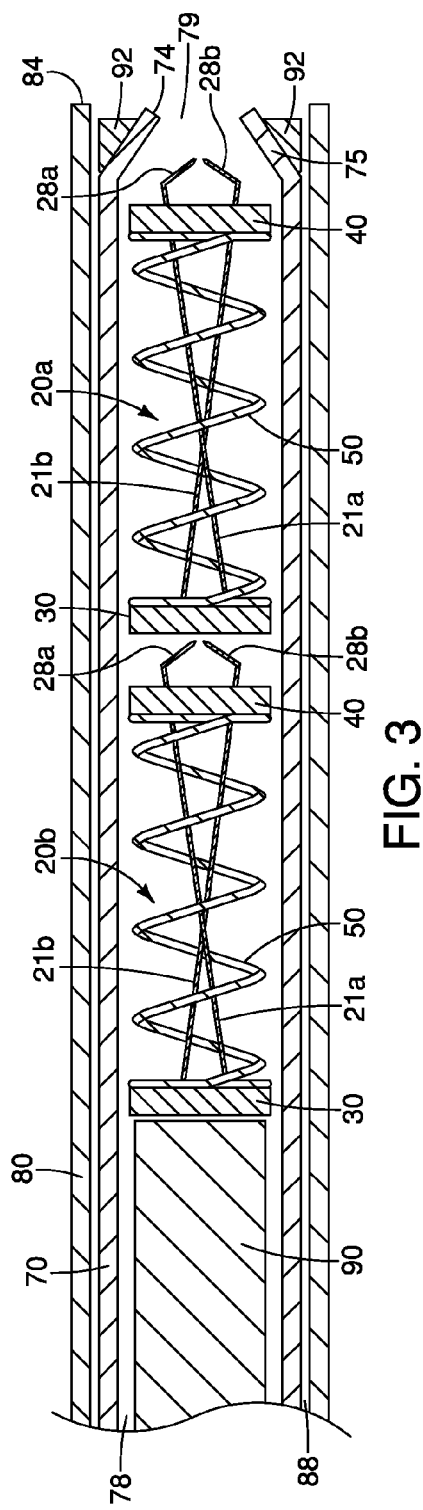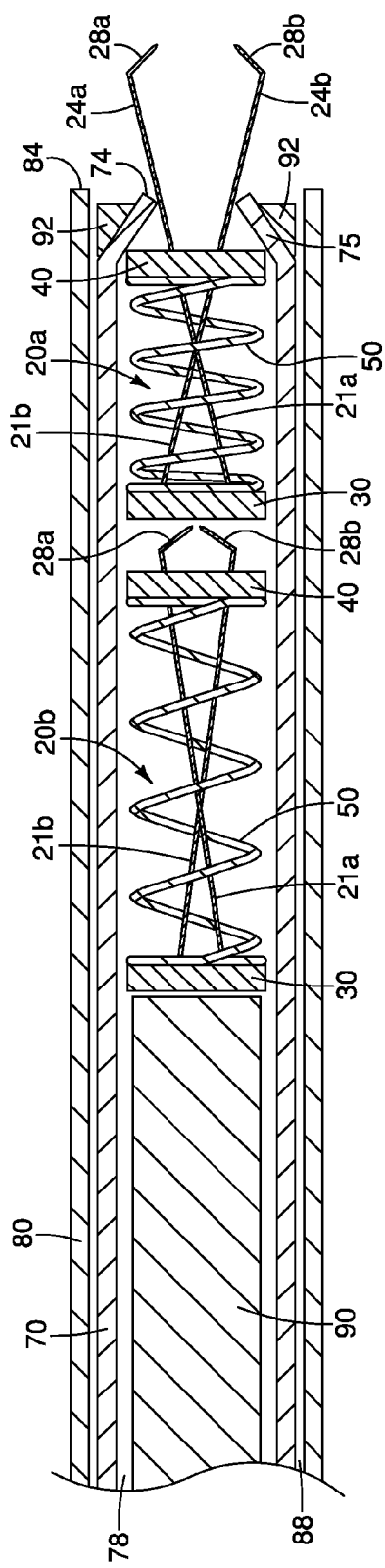

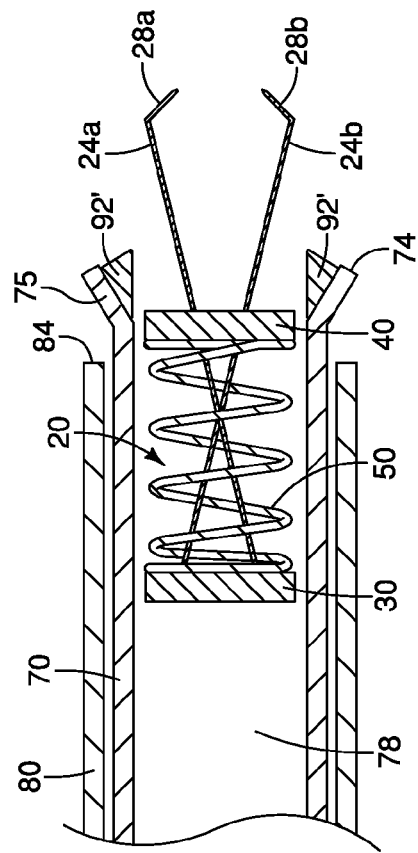
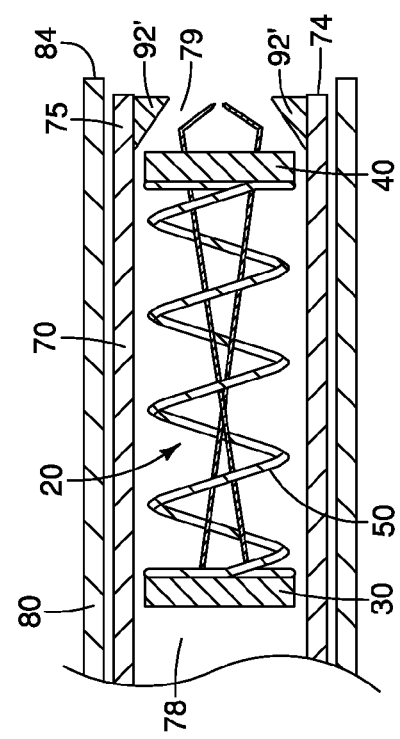

CLIP DEVICES AND METHODS OF DELIVERY AND DEPLOYMENT

PRIORITY CLAIM

This invention claims the benefit of priority of U.S. Provisional Application Ser. No. 61/139,141, entitled "Clip Devices and Methods of Delivery and Deployment," filed Dec. 19, 2008, the disclosure of which is hereby incorporated by reference in its entirety.

BACKGROUND

Conventionally, a clip may be introduced into a body cavity through an endoscope to grasp living tissue of a body cavity for hemostasis, marking, and/or ligating. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding.

Gastrointestinal bleeding is a somewhat common and serious condition that is often fatal if left untreated. This problem has prompted the development of a number of endoscopic therapeutic approaches to achieve hemostasis such as the injection of sclerosing agents and contact thermo-coagulation techniques. Although such approaches are often effective, bleeding continues for many patients and corrective surgery therefore becomes necessary. Because surgery is an invasive technique that is associated with a high morbidity rate and many other undesirable side effects, there exists a need for highly effective, less invasive procedures.

Mechanical hemostatic devices have been used in various parts of the body, including gastrointestinal applications. Such devices are typically in the form of clamps, clips, staples and sutures, which are able to apply sufficient constrictive forces to blood vessels so as to limit or interrupt blood flow. One of the problems associated with conventional hemostatic devices, however, is that many devices are not strong enough to cause permanent hemostasis. Further, typically once such mechanical hemostatic devices are at least partially deployed, they cannot be opened and closed repeatedly before the final release of the device, which may result in possible permanent deployment of the device at an undesirable location.

Still further, mechanical hemostatic devices typically are loaded, one at a time, within an introducer equipped to deliver and deploy the device. A first hemostatic device may be deployed, but if it becomes desirable to deliver and deploy a second hemostatic device, the introducer typically must be removed from the patient's body in order to load the second hemostatic device. The introducer then is loaded back into the patient's body to deploy the second hemostatic device, and the process is repeated for each subsequent device. However, the process of deploying only one hemostatic device at a time may become very time consuming and inconvenient, causing significant delays when it may be imperative to quickly stop bleeding.

SUMMARY

The present embodiments provide a clip device for engaging tissue. The clip device comprises at least first and second arms, each having proximal and distal ends. A spring member is disposed to surround at least a portion of the first and second arms. The clip device comprises an open state when the spring member is in a compressed state in which a distal end of the spring member is spaced apart from the distal ends of the first and second arms. When the spring member is compressed, the distal ends of the first and second arms tend to be spaced apart from each other.

Further, the clip device comprises a closed state when the spring member is in a relaxed state in which the spring member is biased to extend distally towards the distal ends of the first and second arms. When the spring member is relaxed, the distal ends of the first and second arms are urged adjacent to each other. The distal ends the first and second arms may penetrate tissue and promote hemostasis when the clip device is in the closed state.

In one embodiment, the clip device further comprises proximal and distal base members. Proximal and distal ends of the spring member contact the proximal and distal base members, respectively. Further, the spring member is disposed to surround at least a portion of the first and second arms. In this embodiment, the distal base member has an aperture and may slide over the first and second arms. When the spring member is in the relaxed state, the distal base member is advanced distally over the first and second arms and promotes closure of the distal ends of the first and second arms.

A delivery system for deploying at least one clip device may comprise an outer sheath and a catheter, each having a lumen. The catheter is configured for longitudinal movement within the lumen of the outer sheath, and multiple clip devices are configured to be selectively advanced through the lumen of the catheter. Preferably, at least one wedge member is disposed along a flexible distal region of the catheter. The wedge member is configured to form a constriction at a distal end of the catheter when the outer sheath is positioned over the distal end of the catheter. Distal advancement of a first clip device relative to the constriction is configured to cause the distal base member of the first clip device to engage the constriction, and further configured to cause the distal ends of the first and second arms to extend beyond the constriction to assume the open state. At this time, the spring member may be held in the compressed state near the distal end of the catheter. Subsequent proximal retraction of the outer sheath, beyond the distal end of the catheter and the wedge member, permits radially outward movement of the distal end of the catheter and the wedge member to thereby remove the constriction and permit deployment of the entire clip device from the distal end of the catheter.

Advantageously, in this manner, any number of clip devices may be sequentially loaded into the lumen of the catheter and deployed, one at a time, without the need to remove the catheter and the outer sheath from the patient's body and individually re-load clip devices, thereby saving important operating time. Further, each of the clip devices advantageously may move between the open and closed states any number of times before final deployment.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 3-5 are side-sectional views illustrating an exemplary delivery system and sequence of deployment for at least one clip device provided in accordance with FIGS. 1-2.

FIGS. 7-8 are side-sectional views of an alternative embodiment of a delivery system.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 1:
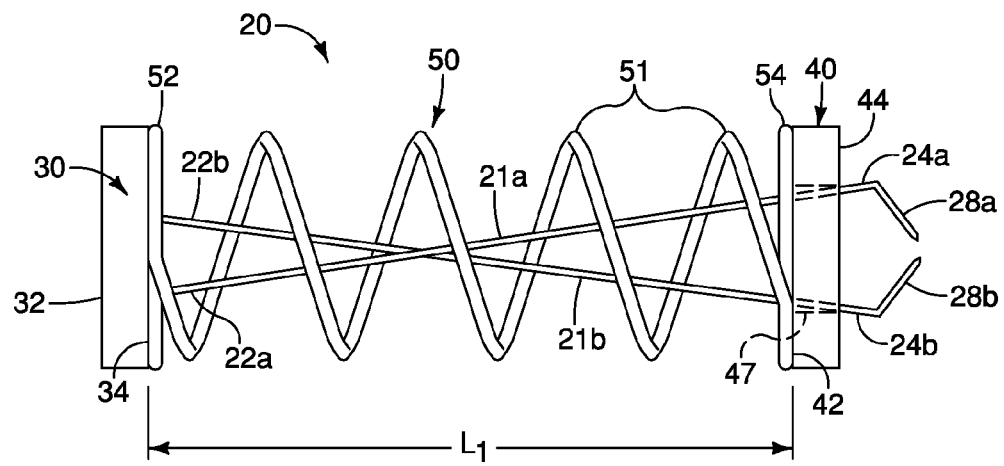
FIG. 1 is a side view of a clip device of a first embodiment in a closed state.

Referring now to FIG. 1, a first embodiment of a clip device 20 is shown. In this embodiment, the clip device 20 comprises a first arm 21a and a second arm 21b. The first arm 21a has a proximal end 22a and a distal end 24a, while the second arm 21b has a proximal end 22b and a distal end 24b. The clip device 20 further comprises a proximal base member 30 having proximal and distal surfaces 32 and 34. Optionally, the clip device 20 may comprise a distal base member 40 having proximal and distal surfaces 42 and 44, and an aperture 47 formed therein, as shown in FIG. 1.

Figure 2:
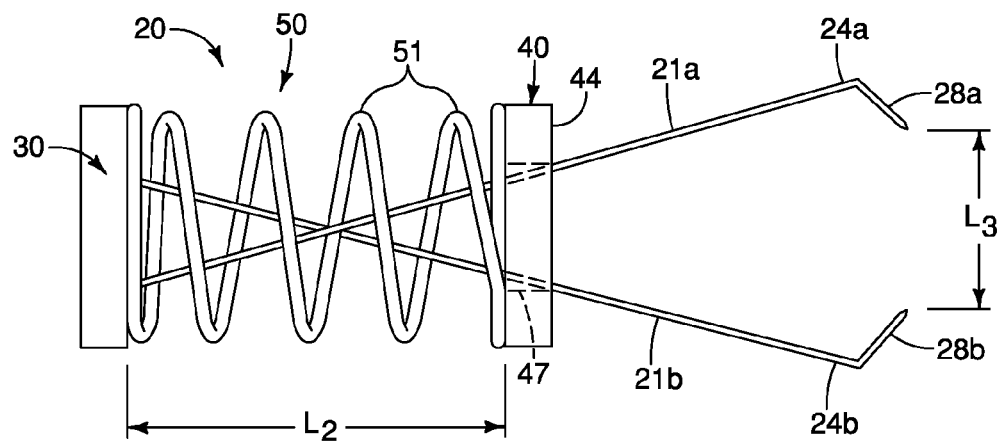
FIG. 2 is a side view of the clip device of FIG. 1 in an open state.

The clip device 20 further comprises a spring member 50 having a proximal end 52, a distal end 54, and a plurality of turns 51 disposed therebetween. The spring member 50 circumferentially surrounds at least a portion of the first and second arms 21a and 21b. In the embodiment of FIGS. 1-2, the spring member 50 is disposed between the proximal and distal base members 30 and 40. In particular, the proximal end 52 of the spring member 50 contacts the distal surface 34 of the proximal base member 30, while the distal end 54 of the spring member 50 contacts the proximal surface 42 of the distal base member 40. The spring member 50 may be secured to the proximal and distal base members 30 and 40 using an adhesive, solder, weld, mechanical attachment device, or any other suitable mechanism. Alternatively, the spring member 50 may be disposed in an abutting relationship with the proximal and distal base members 30 and 40.

As shown in FIG. 1, the proximal end 22a of the first arm 21a contacts the proximal base member 30 at a location spaced apart from the proximal end 22b of the second arm 21b. The first and second arms 21a and 21b are angled with respect to one another and crisscross between their respective proximal and distal ends. By crisscrossing one another, the arms 21a and 22b may be more inclined to move radially outward and apart from one another in an open state, as shown in FIG. 2. However, as will be explained in FIGS. 9-10 below, the arms alternatively may not cross paths with respect to each other.

The distal ends 24a and 24b of the arms 21a and 21b are preferably bent in radially inward directions to form tips 28a and 28b, respectively, as shown in FIGS. 1-2. The tips 28a and 28b are configured to grasp and/or pierce tissue. While two arms 21a and 21b are depicted in the embodiment of FIGS. 1-5, it is contemplated that fewer or greater arms may be used. For example, as explained in FIGS. 9-10 below, an alternative clip device 120 comprises three arms 121a-121c.

The first and second arms 21a and 21b may be made from any suitable resilient material such as stainless steel, nitinol, plastic, and the like. In addition, the arms may have a cross-sectional shape that is round, square, rectangular, triangular, pie-shaped, truncated cone, and the like. The proximal and distal base members 30 and 40 also may be formed from stainless steel, nitinol, plastic, and the like, although the proximal and distal base members 30 and 40 preferably comprise an enhanced rigidity relative to the first and second arms 21a and 21b.

The clip device 20 may be moved between closed and open states by selectively actuating the spring member 50 between relaxed and compressed states, as shown in FIGS. 1-2, respectively. The spring member 50 comprises a first length $L_1$ in the relaxed state, as shown in FIG. 1. In the relaxed state, the spring member 50 is longitudinally expanded and the distal base member 40 may engage the distal ends 24a and 24b of the arms 21a and 21b, thereby urging the distal ends 24a and 24b of the arms 21a and 21b adjacent to one another. At this time, the clip device 20 is in a closed state, in which the arms 21a and 21b are configured for delivery within a lumen 78 of a catheter 70, as shown below. Further, in the closed state of FIG. 1, the tips 28a and 28b are configured to grasp tissue and facilitate tissue closure and hemostasis.

It should be noted that the aperture 47 of the distal base member 40 may be sized so that it will not slide distally over the distal ends 24a and 24b of the arms 21a and 21b when the spring member 50 is relaxed and the clip device 20 is in the closed state of FIG. 1. Optionally, distal stop members, such as a solder, may be disposed on the arms 21a and 22b at a location proximal to the tips 28a and 28b, to limit distal advancement of the distal stop member 40.

The spring member 50 further comprises a second length $L_2$ in the compressed state, as shown in FIG. 2. The second length $L_2$ is less than the first length $L_1$ due to compression of the spring member 50, and therefore, the distal base member 40 is spaced further apart from the distal ends 24a and 24b of the arms 21a and 21b. When the spring member 50 is in the compressed state of FIG. 2, the clip device 20 is in an open state in which the distal ends 24a and 24b of the first and second arms 21a and 21b, and more specifically the tips 28a and 28b, are spaced apart a distance $L_3$ that is configured to at least partially surround one or more desired tissue segments prior to closure of the first and second arms 21a and 21b. In particular, since the distal ends 24a and 24b of the arms 21a and 21b are not radially constrained by the spring member 50 and/or the distal base member 40, the distal ends 24a and 24b of the arms 21a and 21b may move in a radially outward direction, as shown in FIG. 2. The arms may move in a radially outward direction due to inherent resilient properties of the material forming the arms 21a and 21b, or alternatively, the arms 21a and 21b may be heat-set to assume the deployed configuration shown in FIG. 2.

While the distal base member 40 is depicted as approximately halfway between the proximal base member 30 and the distal ends 24a and 24b of the arms 21a and 21b in the open state of FIG. 2, the distal base member 40 may be positioned closer to or further from the proximal base member 30 when the spring member 50 is in a compressed state. For example, if the spring member 50 is further compressed, the second length $L_2$ will be shortened and the spacing $L_3$ may be increased. By contrast, if the spring member 50 is further expanded, the second length $L_2$ will be increased and the spacing $L_3$ may be reduced.

The spring member 50 may comprise any suitable material, such as stainless steel. Further, the spring member 50 may comprise a shape and configuration that may be tailored based on a given application. In particular, the diameter, wire thickness, stiffness and/or other features of the spring member 50 may be varied as needed for a particular procedure to meet anatomical constraints and/or vary the force imposed on tissue segments. For example, a substantially stiff spring member 50 may provide an increased force upon the distal ends 24a and 24b of the arms 21a and 21b to reduce the likelihood of the clip device 20 becoming disengaged from tissue after deployment.

In the embodiment of FIGS. 1-2, the proximal and distal base members 30 and 40 comprise generally cylindrical shapes, which may facilitate insertion through a lumen 78 of a catheter 70, as explained further below. However, the proximal and distal base members 30 and 40 alternatively may comprise different shapes. Further, as will be explained further below, the distal base member 40 preferably comprises an outer diameter sized to selectively engage a constriction 79 of the catheter 70, but the proximal base member 30 and the spring member 50 may comprise reduced diameter profiles relative to the distal base member 40.

Figure 5:
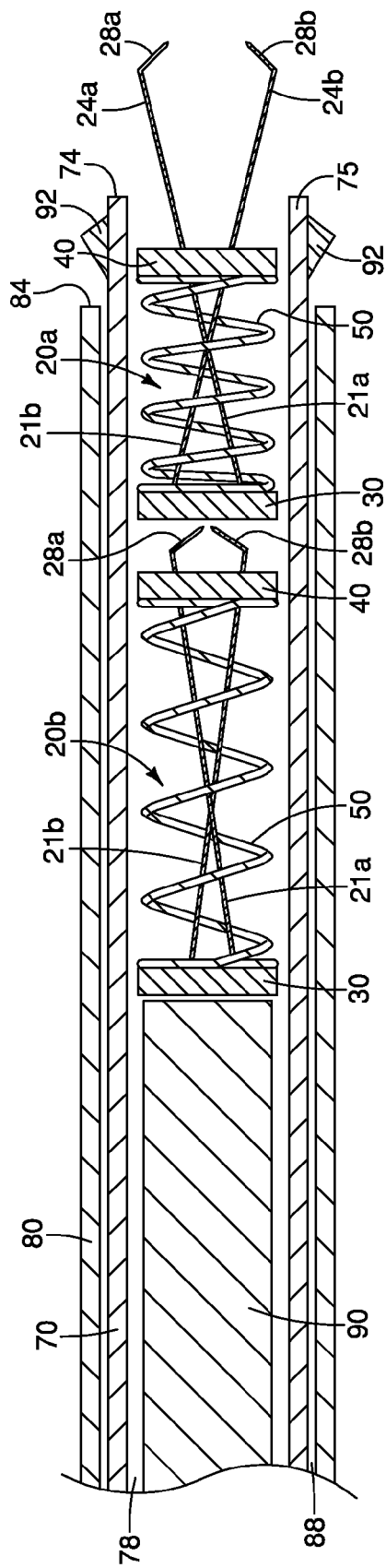

Referring now to FIGS. 3-5, an exemplary system is described for delivery and deployment of at least one of the clip devices 20 of FIGS. 1-2. The delivery system comprises a catheter 70 having a lumen 78, and further comprises an outer sheath 80 having a lumen 88. In the embodiment of FIGS. 3-5, first and second clip devices 20a and 20b are provided for sequential deployment.

The catheter 70 comprises an outer diameter that is less than an inner diameter of the outer sheath 80, thereby allowing the catheter 70 to be longitudinally advanced within the lumen 88 of the outer sheath 80. The catheter 70 further comprises an inner diameter that is generally larger than an outer diameter of the first and second clip devices 20a and 20b, thereby allowing the first and second clip devices 20a and 20b to be loaded within the lumen 78 of the catheter 70, as shown in FIG. 3.

Figure 6:
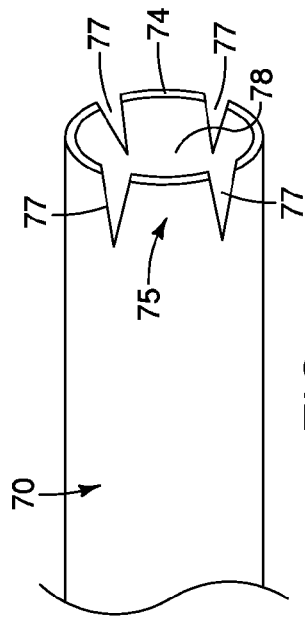
FIG. 6 is a perspective view illustrating features of a distal region of a catheter of a delivery system.

The catheter 70 comprises a distal end 74 and a flexible distal region 75. The flexible distal region 75 may be selectively moved in radially inward and outward directions, for purposes described further below. Preferably, a plurality of slits 77 are formed in the distal end 74, as shown in FIG. 6, to permit the radial flexibility along the distal region 75.

At least one wedge member 92 may be used to form a constriction 79 at the distal end 74 of the catheter 70. In the embodiment of FIGS. 3-5, the at least one wedge member 92 has a triangular shape are is disposed between the catheter 70 and the outer sheath 80, causing the flexible distal region 75 of the catheter 70 to move radially inward to form the constriction 79, as shown in FIGS. 3-4. The wedge member 92 may comprise a biocompatible glue, plastic, metal or other suitable material, and may comprise other shapes besides the triangular shape depicted to accomplish the objectives described below. Alternatively, one or more wedge members 92 may be formed as an integral portion of the catheter 70 at the distal region 75.

The outer sheath 80 may comprise a rigid or substantially rigid material, such as stainless steel or plastic materials, which substantially prohibits radial outward movement of the wedge member 92 and the flexible distal region 75 of the catheter 70, when a distal end 84 of the outer sheath 80 covers these regions, as shown in FIGS. 3-4. However, when the distal end 84 of the outer sheath 80 is retracted proximally beyond the wedge member 92 and the flexible distal region 75 of the catheter 70, the flexible distal region 75 may move radially outward and the constriction 79 may be removed, as depicted in FIG. 5 below.

In one exemplary method, the first and second clip devices 20a and 20b may be loaded sequentially such that the first clip device 20a is loaded distal to the second clip device 20b within the lumen 78 of the catheter 70, as shown in FIG. 3. A stylet 90 may be positioned in the lumen 78 at a location proximal to the second clip device 20b. It should be noted that while two clip devices are shown in this example, any number may be used and sequentially loaded into the catheter 70 in an abutting manner distal to the stylet 90.

The outer sheath 80 is positioned over the catheter 70 such that the constriction 79 is formed via the wedge member 92, as shown in FIG. 3. The constriction 79 forms an inner diameter that is less than an outer diameter of the distal base member 40, as shown in FIG. 3. Accordingly, the distal base member 40 cannot be advanced through the distal end 74 of the catheter 70. When the spring member 50 of the first clip device 20a is in the relaxed state shown in FIG. 3, the distal ends 24a and 24b of the arms 21a and 21b may extend partially into the constriction 79, but preferably do not extend beyond the distal end 74 of the catheter 70 to reduce the likelihood of inadvertent piercing.

Referring to FIG. 4, in a next step, the stylet 90 is advanced distally, relative to the catheter 70 and the outer sheath 80, to cause distal advancement of the second clip device 20b and corresponding distal advancement of the first clip device 20a in an abutting manner. The stylet 90 is advanced while the outer sheath 80 continues to cover the distal end 74 of the catheter 70, thereby retaining the constriction 79. As the first clip device 20a is advanced distally, the distal base member 40 of the first clip device 20a is retained by the constriction 79. However, the proximal base member 30 and the arms 21a and 21b of the first clip device 20a are advanced distally relative to the constriction 79, and the spring member 50 becomes compressed between the proximal and distal base members 30 and 40, as depicted in FIG. 4. At this time, the distal ends 24a and 24b of the arms 21a and 21b of the first clip device 20a are advanced distally beyond the distal end 74 of the catheter 70, and when unconstrained, tend to bow in a radially outward direction spaced apart from one another. The spacing $L_3$ shown in FIG. 2 therefore is formed between the distal ends 24a and 24b of the first and second arms 21a and 21b. The length of the spacing $L_3$ may be varied based on the amount of distal advancement of the stylet 90 and corresponding compression of the spring member 50. Further, the length of the spacing $L_3$ may be sufficient to capture one or more desired segments of tissue between the distal tips 28a and 28b of the arms 21a and 21b.

In accordance with one aspect, a physician need not deploy the first clip device 20a at this time, even through the first clip device 20a is in the open state. Rather, the first clip device 20a may be moved between the open and closed states, shown in FIGS. 3-4, any number of times before final deployment. For example, if it becomes desirable to recapture the distal ends 24a and 24b of the arms 21a and 21b when in the open state of FIG. 4, a physician may proximally retract the stylet 90, which reduces the force upon the spring member 50 of the first clip device 20a. The spring member 50 assumes the relaxed state shown in FIG. 3, and the proximal base member 30 and the arms 21a and 21b move in a proximal direction, causing the distal ends 24a and 24b of the arms 21a and 21b to move in radially inward directions back into the catheter 70. Advantageously, in this manner, each of the individual clip devices may move between the open and closed states any number of times before final deployment.

Referring now to FIG. 5, in a next step, if the physician wishes to proceed with deployment of the first clip device 20a in the open state of FIG. 4, the outer sheath 80 is proximally retracted with respect to the catheter 70, such that the distal end 84 of the outer sheath 80 is positioned proximal to the wedge member 92. At this time, the wedge member 92 is no longer radially constrained and may move in a radially outward direction, as shown in FIG. 5. The flexible distal region 75 of the catheter 70 also may move radially outward and the constriction 79 may be removed, as depicted in FIG. 5. In this configuration, an inner diameter at the distal end 74 of the catheter 70 is equal to or greater than the outer diameter of the first clip device 20a. Therefore, the first clip device 20a may be ejected from the distal end 74 of the catheter 70. It should be noted that, when no longer constrained by the constriction 79, the spring member 50 is biased towards the relaxed state of FIG. 1 and the distal base member 40 is advanced towards the distal ends 24a and 24b of the arms 21a and 21b, causing the tips 28a and 28b to securely engage tissue, e.g., to promote hemostasis. The second clip device 20b then is positioned for deployment near the distal end 74 of the catheter 70.

After deployment of the first clip device 20a, but before deployment of the second clip device 20b, the outer sheath 80 may be distally advanced with respect to the catheter 70, thereby urging the wedge member 92 in a radially inward direction and causing the flexible distal region 75 to move radially inward and form the constriction 79, as shown in FIG. 3 above. Subsequently, the same sequence of deployment for the first clip device 20a, as explained with respect to FIGS. 3-5, may be used to deploy the second clip device 20b. Advantageously, in this manner, any number of clip devices may be sequentially loaded into the lumen 78 of the catheter 70 and deployed, one at a time, without the need to remove the catheter 70 and outer sheath 80 from the patient's body and individually re-load clip devices thereby saving important operating time.

It should be noted that the distal base member 40 optionally may be omitted. In this case, substantially identical method steps may be used to deploy the first and second clip devices 20a and 20b, however, the distal end 54 of the spring member 50 would be configured to be retained by the constriction 79 of the catheter 70, and further configured to directly apply a compressive force directly upon the distal ends 24a and 24b of the arms 21a and 21b in the closed state of FIG. 1.

Referring to FIG. 6, and as noted above, the flexible distal region 75 of the catheter 70 may be selectively moved in a radially inward and outward direction by providing a plurality of slits 77 formed in the flexible distal region 75. In the embodiment shown, four slits 77 are formed in the distal end 74 of the catheter 70 and extend in tapered manner in a distal to proximal direction. The four slits 77 may be radially spaced apart around the circumference of the catheter 70. One or more of the wedge members 92 may be attached to the flexible distal region 75 at one or more locations between the slits 77. While four illustrative tapered slits 77 are shown in FIG. 6, it will be appreciated that greater or fewer slits may be employed, and they may comprise different shapes and configurations than depicted.

Referring now to FIGS. 7-8, the clip device 20 is deployed in the same manner as FIGS. 3-5, with the main exception that one or more alternative wedge members 92' are disposed internal to the catheter 70. Preferably, the alternative wedge members 92' comprise a triangular shape and are attached to an inner surface of the catheter 70 along the flexible distal region 75, or are formed integrally with the distal region 75. When the outer sheath 80 is distally advanced to cover the distal end 74 of the catheter 70, the wedge member 92' is moved radially inward to form the constriction 79, as shown in FIG. 7. At this time, the spring member 50 of the clip device 20 may be compressed by distal advancement of the stylet 90, as explained in FIG. 4 above.

When it becomes desirable to release the clip device 20, the outer sheath 80 may be proximally retracted with respect to the catheter 70 to a location proximal to the wedge member 92'. At this time, the wedge member 92' is no longer radially constrained and may move in a radially outward direction to form a substantially flush extension to the catheter 70, while the flexible distal region 75 moves radially outward, as shown in FIG. 8. At this time, the constriction 79 is removed and the clip device 20 may be ejected from the distal end 74 of the catheter 70.

Figure 9:
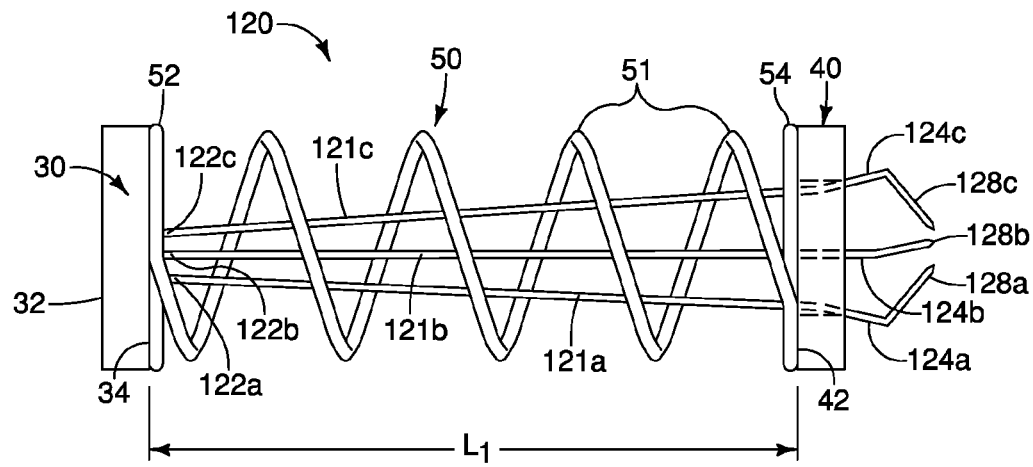
FIG. 9 is a side view of an alternative clip device in a closed state.
Figure 10:
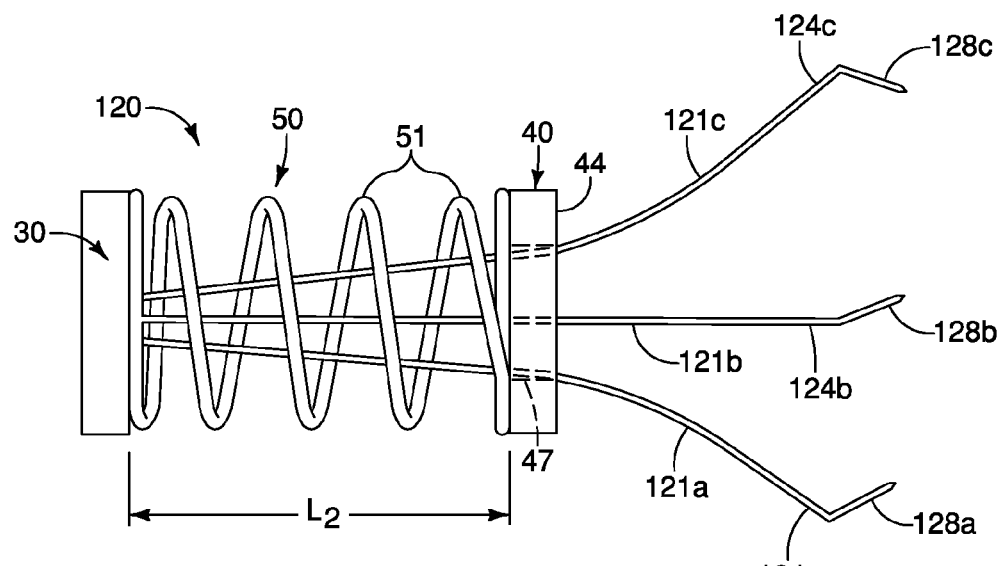
FIG. 10 is a side view of the clip device of FIG. 9 in an open state.

Referring now to FIGS. 9-10, an alternative clip device 120 is shown. The clip device 120 is substantially identical to the clip device 20 of FIGS. 1-5, with the main exceptions that the clip device 120 comprises three arms 121a-121c having proximal ends 122a-122c and distal ends 124a-124c, respectively. Unlike the embodiment of FIGS. 1-5, the arms 121a-121c do not cross paths with each other between their respective proximal and distal ends. Distal tips 128a-128c of the three arms 121a-121c tend to be radially spaced apart when the clip device 120 is in the open state, as shown in FIG. 10. The distal ends 124a-124c of the arms 121a-121c may be biased to assume the open state of FIG. 10, either due to the inherent resilient properties of the material forming the arms 121a-121c, or alternatively, the arms 121a-121c may be heat-set to assume the deployed configuration shown in FIG. 10. Preferably, the alternative clip device 120 is deployed in an identical manner to the clip device 20, as described with respect to FIGS. 3-5 above.

In further alternative embodiments, the apparatus and methods described herein may be used for engaging a layer of material, and are not restricted to methods for treatment of a human or animal body by surgery or therapy. For example, first and second clip devices may be provided and loaded within a lumen of a catheter, as described above. The first clip device may be positioned to engage a layer of material at a desired location in the open state, and then a compressive force is removed to allow the first spring member to be biased towards the relaxed state and cause the distal ends of the first and second arms of the first clip device to be adjacent to each other and engage the layer of material, as generally described above.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A clip device for engaging tissue, the clip device comprising:

a first arm having proximal and distal ends;

a second arm having proximal and distal ends;

a proximal base member directly contacting the proximal ends of the first and second arms; and a spring member having proximal and distal ends, wherein the spring member is disposed to surround at least a portion of the first and second arms, and wherein the proximal end of the spring member is attached to the proximal base member, wherein the clip device comprises an open state when the spring member is in a compressed state in which the distal end of the spring member is spaced apart from the distal ends of the first and second arms, and wherein the distal ends of the first and second arms tend to be spaced apart from each other when the clip device is in the open state, wherein the clip device comprises a closed state when the spring member is in a relaxed state in which the spring member is biased to extend distally towards the distal ends of the first and second arms, wherein the distal ends of the first and second arms are adjacent to each other when the clip device is in the closed state, wherein the relaxed state of the spring member causes the arms to close.

2. The clip device of claim 1 further comprising a distal base member having an aperture configured to permit movement of the distal base member at least partially over the first and second arms, wherein the distal end of the spring member contacts a proximal surface of the distal base member.

3. The clip device of claim 1, wherein the distal ends the first and second arms are bent in radially inward directions to form tips configured to penetrate tissue.

4. The clip device of claim 1, wherein the first and second arms are angled with respect to one another and crisscross between their respective proximal and distal ends.

5. The clip device of claim 1 further comprising a third arm having proximal and distal ends, wherein the first, second and third arms tend to be spaced apart from each other when the clip device is in the open state, wherein the distal ends of the first, second and third arms are adjacent to each other when the clip device is in the closed state, and wherein the first, second and third arms do not cross paths with respect to each other when the clip device is in the open state.

6. The clip device of claim 1 further comprising:
a catheter having a lumen, wherein the clip device is configured to be selectively advanced through the lumen of the catheter; and
a constriction formed at a distal end of the catheter, wherein the constriction facilitates selective deployment of the clip device through the distal end of the catheter.

7. The clip device of claim 6, wherein multiple clip devices are configured to be loaded in a sequential manner within the lumen of the catheter at the same time, and further are configured to be individually and selectively deployed from the distal end of the catheter.

8. The clip device of claim 6 further comprising:
an outer sheath having a lumen, wherein the catheter is configured for longitudinal movement within the lumen of the outer sheath; and
at least one wedge member disposed along a flexible distal region of the catheter, wherein the wedge member forms the constriction at the distal end of the catheter when the outer sheath is positioned over the distal end of the catheter.

9. The clip device of claim 8, further comprising:
a distal base member having an aperture configured to permit movement of the distal base member at least partially over the first and second arms, wherein the distal end of the spring member contacts a proximal surface of the distal base member, and
wherein the constriction comprises a diameter smaller than an outer diameter of the distal base member, such that distal advancement of the clip device relative to the constriction is configured to cause the distal base member to engage the constriction, and further configured to cause the distal ends of the first and second arms to extend distally beyond the distal end of the catheter and assume the open state, and further cause the spring member to assume the compressed state.

10. The clip device of claim 9, wherein proximal retraction of the outer sheath, beyond the distal end of the catheter and the wedge member, is adapted to permit radially outward movement of the distal end of the catheter and the wedge member to thereby remove the constriction and permit deployment of the entirety of the clip device from the distal end of the catheter.

11. The clip device of claim 1 wherein the first and second arms are attached to the proximal base member.

12. The clip device of claim 1 wherein the first and second arms are discrete from the proximal base member.

13. A clip device for engaging tissue, the clip device comprising:
a first arm having proximal and distal ends;
a second arm having proximal and distal ends;
a proximal base member contacting the proximal ends of the first and second arms;
a spring member having proximal and distal ends, wherein the spring member is disposed to surround at least a portion of the first and second arms, and wherein the proximal end of the spring extends from the proximal base member; and
a distal base member having an aperture configured to permit movement of the distal base member at least partially over the first and second arms, wherein the distal end of the spring member contacts a proximal surface of the distal base member,
wherein the clip device comprises an open state when the spring member is in a compressed state in which the distal end of the spring member is spaced apart from the distal ends of the first and second arms, and wherein the distal ends of the first and second arms tend to be spaced apart from each other when the clip device is in the open state, and
wherein the clip device comprises a closed state when the spring member is in a relaxed state in which the spring member is biased to extend distally towards the distal ends of the first and second arms, wherein the distal ends of the first and second arms are adjacent to each other when the clip device is in the closed state.

14. The clip device of claim 13, wherein the distal ends the first and second arms are bent in radially inward directions to form tips configured to penetrate tissue.

15. The clip device of claim 13, wherein the first and second arms are angled with respect to one another and crisscross between their respective proximal and distal ends.

16. The clip device of claim 13 further comprising:
a catheter having a lumen, wherein the clip device is configured to be selectively advanced through the lumen of the catheter; and
a constriction formed at a distal end of the catheter, wherein the constriction facilitates selective deployment of the clip device through the distal end of the catheter.

17. The clip device of claim 16, wherein multiple clip devices are configured to be loaded in a sequential manner within the lumen of the catheter at the same time, and further are configured to be individually and selectively deployed from the distal end of the catheter.

18. The clip device of claim 16 further comprising:
an outer sheath having a lumen, wherein the catheter is configured for longitudinal movement within the lumen of the outer sheath; and
at least one wedge member disposed along a flexible distal region of the catheter, wherein the wedge member forms the constriction at the distal end of the catheter when the outer sheath is positioned over the distal end of the catheter.

19. The clip device of claim 18, wherein the constriction comprises a diameter smaller than an outer diameter of the distal base member, such that distal advancement of the clip device relative to the constriction is configured to cause the distal base member to engage the constriction, and further configured to cause the distal ends of the first and second arms to extend distally beyond the distal end of the catheter and assume the open state, and further cause the spring member to assume the compressed state.

20. The clip device of claim 19, wherein proximal retraction of the outer sheath, beyond the distal end of the catheter and the wedge member, is adapted to permit radially outward movement of the distal end of the catheter and the wedge member to thereby remove the constriction and permit deployment of the entirety of the clip device from the distal end of the catheter.

* * * * *

UNITED STATES PATENT AND TRADEMARK OFFICE
CERTIFICATE OF CORRECTION

PATENT NO.         : 8,491,610 B2                           Page 1 of 1
APPLICATION NO.    : 12/638190
DATED              : July 23, 2013
INVENTOR(S)        : John A. Karpiel et al.

It is certified that error appears in the above-identified patent and that said Letters Patent is hereby corrected as shown below:

In the Claims

In column 9, claim 1, line 3, after "of the first and second" replace "aims" with --arms--.

Signed and Sealed this
Sixth Day of May, 2014

Michelle K. Lee
*Deputy Director of the United States Patent and Trademark Office*